(12) United States Patent
Linderman et al.

(10) Patent No.: US 8,771,278 B2
(45) Date of Patent: *Jul. 8, 2014

(54) SYSTEMS AND METHODS FOR VERTEBRAL OR OTHER BONE STRUCTURE HEIGHT RESTORATION AND STABILIZATION

(75) Inventors: Evan D. Linderman, Northbrook, IL (US); John A. Krueger, Muskego, WI (US)

(73) Assignee: CareFusion 2200, Inc., San Diego, CA (US)

( * ) Notice: Subject to any disclaimer, the term of this patent is extended or adjusted under 35 U.S.C. 154(b) by 13 days.

This patent is subject to a terminal disclaimer.

(21) Appl. No.: 13/547,859

(22) Filed: Jul. 12, 2012

(65) Prior Publication Data

US 2012/0277753 A1 Nov. 1, 2012

Related U.S. Application Data

(63) Continuation of application No. 12/615,573, filed on Nov. 10, 2009, now Pat. No. 8,226,657.

(51) Int. Cl.
*A61F 2/46* (2006.01)
*A61B 17/88* (2006.01)

(52) U.S. Cl.
USPC ........................................ 606/86 R; 606/279

(58) Field of Classification Search
USPC .................... 606/86 R, 279, 92–94
See application file for complete search history.

(56) References Cited

U.S. PATENT DOCUMENTS

| | | |
|---|---|---|
| 4,399,814 A * | 8/1983 | Pratt et al. ........................ 606/94 |
| 4,969,888 A | 11/1990 | Scholten et al. |
| 5,047,015 A | 9/1991 | Foote et al. |
| 5,091,205 A | 2/1992 | Fan |
| 5,108,404 A | 4/1992 | Scholten et al. |
| 5,201,753 A | 4/1993 | Lampropoulos et al. |
| 5,209,732 A | 5/1993 | Lampropoulos et al. |
| 5,827,289 A | 10/1998 | Reiley et al. |
| 5,849,014 A | 12/1998 | Mastrorio et al. |
| 5,972,015 A | 10/1999 | Scribner et al. |
| 6,066,154 A | 5/2000 | Reiley et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,280,456 B1 | 8/2001 | Scribner et al. |
| 6,423,083 B2 | 7/2002 | Reiley et al. |
| 6,605,056 B2 | 8/2003 | Eidenschink et al. |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,632,235 B2 | 10/2003 | Weikel et al. |
| 6,641,587 B2 | 11/2003 | Scribner et al. |
| 6,663,647 B2 | 12/2003 | Reiley et al. |
| 6,716,216 B1 | 4/2004 | Boucher et al. |
| 6,726,691 B2 | 4/2004 | Osorio et al. |
| 6,852,095 B1 | 2/2005 | Ray |
| 6,899,719 B2 | 5/2005 | Reiley et al. |

(Continued)

*Primary Examiner* — Anu Ramana
(74) *Attorney, Agent, or Firm* — Brinks Gilson & Lione

(57) ABSTRACT

A method for stabilizing fractured bone structure having a fractured height includes expanding the bone structure to a restored height greater than the fractured height by transitioning an expandable member inserted into the bone structure from a contracted state to an expanded state. A curable material is delivered into a cavity formed in the bone structure and allowed to harden while the expandable member maintains the bone structure at the restored height. The expandable member is then removed from the bone structure.

7 Claims, 10 Drawing Sheets

(56) References Cited

U.S. PATENT DOCUMENTS

| | | |
|---|---|---|
| 6,923,813 B2 | 8/2005 | Phillips et al. |
| 6,979,341 B2 | 12/2005 | Scribner et al. |
| 6,981,981 B2 | 1/2006 | Reiley et al. |
| 7,044,954 B2 | 5/2006 | Reiley et al. |
| 7,153,306 B2 | 12/2006 | Ralph et al. |
| 7,156,861 B2 | 1/2007 | Scribner et al. |
| 7,166,121 B2 | 1/2007 | Reiley et al. |
| 7,241,303 B2 | 7/2007 | Reiss et al. |
| 7,252,671 B2 | 8/2007 | Scribner et al. |
| 7,261,720 B2 | 8/2007 | Stevens et al. |
| 7,563,265 B1 | 7/2009 | Murphy |
| 2002/0026195 A1 | 2/2002 | Layne et al. |
| 2004/0167562 A1 | 8/2004 | Osorio et al. |
| 2006/0095064 A1 | 5/2006 | Scribner et al. |
| 2006/0235460 A1 | 10/2006 | Reiley et al. |
| 2006/0276819 A1 | 12/2006 | Osorio et al. |
| 2007/0010845 A1 | 1/2007 | Gong et al. |
| 2007/0021769 A1 | 1/2007 | Scribner et al. |
| 2007/0142842 A1 | 6/2007 | Krueger et al. |
| 2007/0198024 A1 | 8/2007 | Plishka et al. |
| 2008/0058823 A1 | 3/2008 | Reiley et al. |
| 2008/0140083 A1 | 6/2008 | Reiley et al. |
| 2009/0076517 A1 | 3/2009 | Reiley et al. |
| 2009/0088788 A1 | 4/2009 | Mouw |
| 2009/0131950 A1 | 5/2009 | Liu et al. |
| 2009/0204120 A1 | 8/2009 | Trosken et al. |

\* cited by examiner

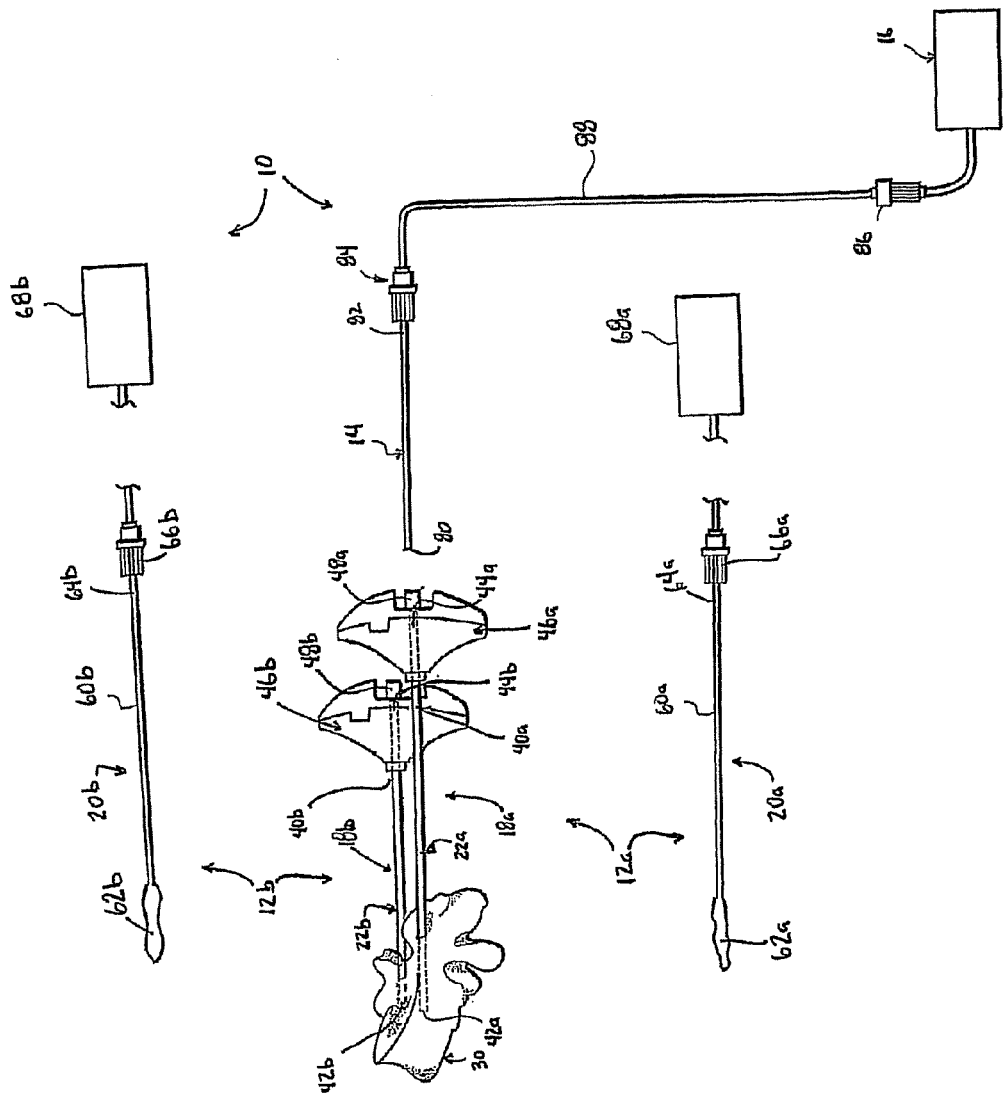

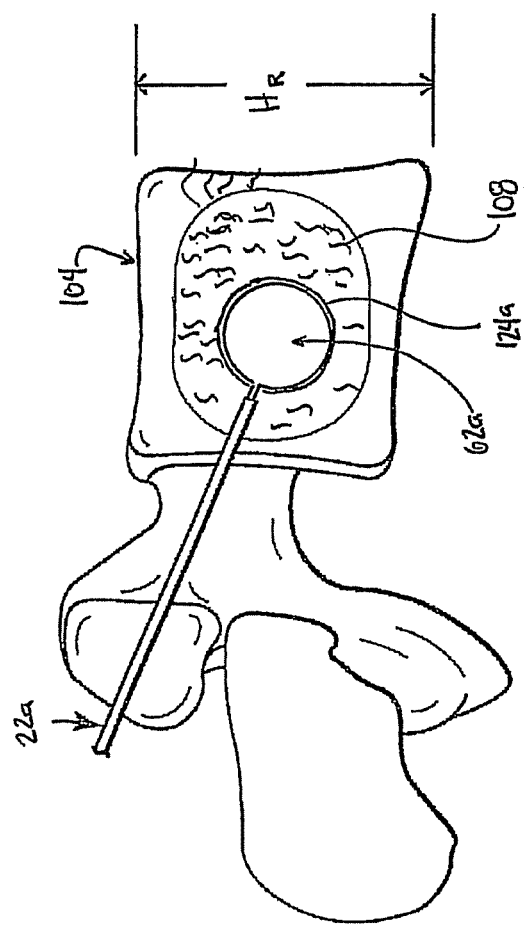

SYSTEMS AND METHODS FOR VERTEBRAL OR OTHER BONE STRUCTURE HEIGHT RESTORATION AND STABILIZATION

CROSS-REFERENCE TO RELATED APPLICATIONS

This application is a continuation of U.S. patent application Ser. No. 12/615,573, filed Nov. 10, 2009, and entitled "Systems and Methods for Vertebral or Other Bone Structure Height Restoration and Stabilization"; and the entire teachings of which are incorporated herein by reference.

BACKGROUND

The present disclosure relates to systems and methods for stabilizing bone structures. More particularly, it relates to systems and methods for stabilizing, and restoring the height of, a bone structure, such as a vertebral body.

Surgical intervention of damaged or compromised bone sites has proven highly beneficial for patients, for example patients with back pain associated with vertebral damage.

Bones of the human skeletal system include mineralized tissue that can be generally categorized into two morphological groups: "cortical" bone and "cancellous" bone. Outer walls of all bones are composed of cortical bone, which is a dense, compact bone structure characterized by a microscopic porosity. Cancellous or "trabecular" bone forms the interior structure of bones. Cancellous bone is composed of a lattice of interconnected slender rods and plates known by the term "trabeculae".

During certain bone-related procedures, cancellous bone is supplemented by an injection of a palliative (or curative) material employed to stabilize the trabeculae. For example, superior and inferior vertebrae in the spine can be beneficially stabilized by the injection of an appropriate, curable material (e.g., PMMA or other bone cement or bone curable material). In other procedures, percutaneous injection of stabilization material into vertebral compression fractures, by, for example, transpedicular or parapedicular approaches, has proven beneficial in relieving pain and stabilizing damaged bone sites. Such techniques are commonly referred to as vertebroplasty.

A conventional vertebroplasty technique for delivering the bone stabilizing material entails placing a cannula with an internal stylet into the targeted delivery site. The cannula and stylet are used in conjunction to pierce the cutaneous layers of a patient above the hard tissue to be supplemented, then to penetrate the hard cortical bone of the vertebra, and finally to traverse into the softer, cancellous bone underlying the cortical bone. Once positioned in the cancellous bone, the stylet is removed, leaving the cannula in the appropriate position for delivery of curable material that in turn reinforces and solidifies the target site.

In some instances, an effectiveness of the procedure can be enhanced by forming a cavity or void within the cancellous bone, and then depositing the curable material in the cavity. For example, a balloon or other expandable device can be initially deployed and then expanded. This action, in turn, compresses cancellous bone to form a cavity, and may also cause a "height" of the bone to increase. As a point of reference, vertebroplasty is a common treatment for a fractured vertebral body, and the height of a fractured vertebral body is oftentimes significantly less than a native or natural height. It has been postulated that the height of a fractured vertebral body can be restored or elevated to a near-normal state when subjected to internal expansion via a balloon or other expandable member. The mechanics of height restoration in conjunction with vertebroplasty stabilization is currently unclear at best. For example, conventional techniques employ a bipedicular approach in which two balloons are inserted into the vertebral body and inflated, resulting in an increase in height (and the cavity or cavities described above). The sequence of subsequent deflation and delivery of curable material is not well documented.

In light of the above, there exists a need in the medical device field for improved systems and methods for restoring the height of, and stabilizing, a fractured vertebral body or other bone structure.

SUMMARY

Some aspects in accordance with principles of the present disclosure relate to a method for stabilizing a fractured bone structure of a patient. The fractured bone structure has a fractured height. The method includes expanding the bone structure to a restored height that is greater than the fractured height by expanding at least a first expandable member from a contracted state to an expanded state. While the expandable member maintains the bone structure at the restored height, a curable material is delivered into a cavity formed in the bone structure. The delivered material is allowed to harden while the expandable member continues to maintain the bone structure at the restored height. The expandable member is then removed from the bone structure. In some embodiments, a second cavity is defined in the bone structure by the removed expandable member, and the curable material is then delivered into the second cavity.

BRIEF DESCRIPTION OF THE DRAWINGS

FIG. 1 is an exploded view of a curable material delivery and height restoration system in accordance with principles of the present disclosure;

FIGS. 3A-6 illustrate the system of FIG. 1 in further performing the height restoration and curable material delivery procedures of the present disclosure.

DETAILED DESCRIPTION

Figure 2A:
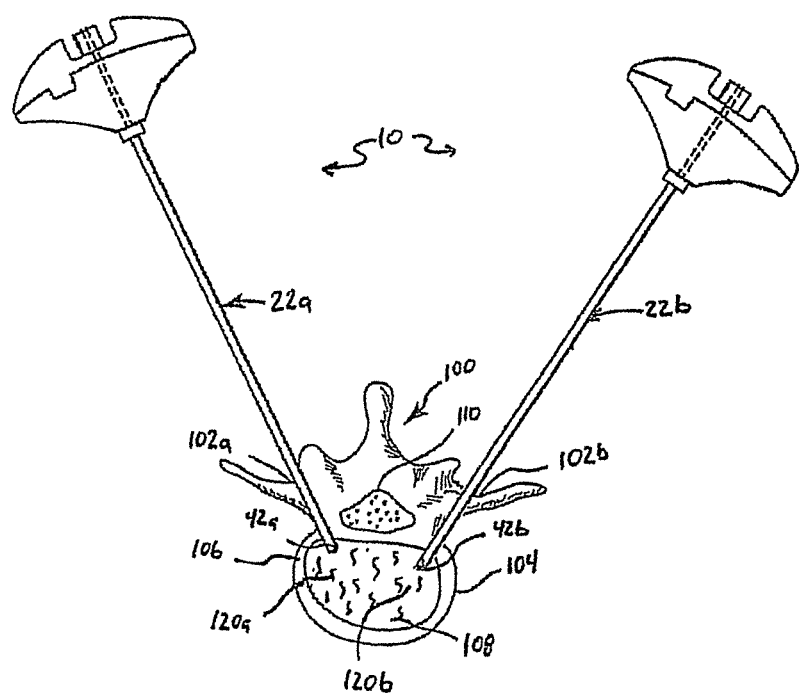
FIGS. 2A and 2B illustrate initial use of the system of FIG. 1 in performing a height restoration and curable material delivery procedure relative to a vertebra, with the vertebra being shown from a superior perspective.

One embodiment of a curable material delivery and height restoration system 10 in accordance with principles of the present disclosure is shown in FIG. 1. The system 10 includes a first delivery assembly 12a, a second delivery assembly 12b, and at least one source of curable material 16. The delivery assemblies 12a, 12b can be substantially identical, and each includes a cannula device 18a, 18b and a cavity-forming device 20a, 20b. Details on the various components are provided below. In general terms, however, the cannula devices 18a, 18b each include a cannula 22a, 22b for insertion into a bone site of interest in a patient. In the embodiment depicted in FIG. 1, the bone site of interest is a vertebra 30. Once the cannulas 22a, 22b are desirably located relative to the vertebra 30, a portion of each of the cavity-forming devices 20a, 20b are delivered to the vertebra 30 via the corresponding cannula 22a, 22b, and operated to form cavities. The second cavity-forming device 20b (alternatively the first cavity-forming device 20a) is removed, and the source of curable material 16 connected to the second cannula 22b. In this regard, an optional delivery tube 14 can be employed, extending from the source 16 and through the second cannula 22b. Regardless, the curable material source 16 is then operated to deliver curable material to the cavity via the second cannula 22b and/or the delivery tube 14. Subsequently, the first cavity-forming device 20a is removed and the curable material source 16 is connected to the first cannula 22a (for example, via the optional delivery tube 14). The curable material source 16 is operated to deliver curable material into the corresponding cavity. With this approach, the systems and methods of the present disclosure can consistently restore a height of the vertebra (or other bone site) 30 to a normal or near-normal state, and the delivered curable material provides desired stabilization.

The system 10 can be used for a number of different procedures including, for example, vertebroplasty and other bone augmentation procedures in which curable material is delivered to a site within bone, as well as possibly to remove or aspirate material from a site within bone. The system 10 is highly useful for delivering a curable material in the form of a bone curable material. The phrase "curable material" within the context of the substance that can be delivered by the system 10 of the present disclosure described herein is intended to refer to materials (e.g., composites, polymers, and the like) that have a fluid or flowable state or phase and a hardened, solid or cured state or phase. Curable materials include, but are not limited to, injectable bone cements (such as polymethylmethacrylate (PMMA) bone curable material), which have a flowable state wherein they can be delivered (e.g., injected) by a cannula to a site and subsequently cure into hardened, cured material. Other materials such as calcium phosphates, bone in-growth materials, antibiotics, proteins, etc., can be used in place of, or to augment, bone cement (but do not affect an overriding characteristic of the resultant formulation having a flowable state and a hardened, solid, or cured state). This would allow the body to reabsorb the curable material and/or improve the clinical outcome based on the type of filler implant material. While FIG. 1 illustrates a single source of curable material 16, in other embodiments, two (or more) sources can be provided. The sources can contain identical curable material compositions; alternatively, the compositions can differ (e.g., a first source can contain bone cement, while a second source contains a mixture of bone cement and bone in-growth material).

As mentioned above, the cannula devices 18a, 18b can be substantially identical, and each includes the cannula 22a, 22b. The cannula 22a, 22b is provided to be positioned in (or immediately proximate) the target or injection site for delivery of the corresponding cavity-forming device 20a, 20b, as well as curable material. The cannula 22a, 22b is preferably made of a surgical grade of stainless steel, but may be made of known equivalent material(s) that are both biocompatible and substantially non-compliant at the expected operating pressures. The cannulas 22a, 22b each define a proximal region 40a, 40b, a distal end 42a, 42b, and a lumen 44a, 44b (referenced generally), respectively, to allow various equipment such as the cavity-forming device 20a, 20b, the optional delivery tube 14, one or more stylets (not shown), etc., to pass therethrough.

Surrounding the proximal region 40a, 40b of the cannula 22a, 22b is an optional handle 46a, 46b for manipulating the cannula 22a, 22b and connecting the cannula 22a, 22b with one or more of the cavity-forming device 20a, 20b and/or the optional delivery tube 14. In some constructions, the cannula device 18a, 18b can further include a handle connector 48a, 48b serving as a proximal end of the corresponding cannula 22a, 22b. The handle connector 48a, 48b can simply be an extension of the cannula 22a, 22b. Alternatively, the handle connector 48a, 48b can incorporate features forming part of a locking mechanism component of the system 10. For example, the handle connector 48a, 48b can optionally include a luer-lock type of connector, but other known connecting mechanism may be successfully interchanged (e.g., a conventional threaded hole, a threaded locking nut arrangement, etc.). Features of the optional locking mechanism are described in U.S. Publication No. 2007/0198024, the entire teachings of which are incorporated herein by reference.

The cavity-forming devices 20a, 20b are substantially identical and can assume various forms appropriate for forming a void or cavity within bone. In this regard, each of the cavity-forming devices 20a, 20b includes an elongated body 60a, 60b distally connected to or forming a working end 62a, 62b. The elongated body 60a, 60b is sized to be slidably inserted within the lumen 44a, 44b of the corresponding cannula 22a, 22b, and can include one or more tubes, shafts, etc., necessary for operation of the corresponding working end 62a, 62b. Regardless, a proximal region 64a, 64b of the elongated body 60a, 60b is optionally connected to or forms a cannula connector 66a, 66b. The cannula connector 66a, 66b can assume various forms conducive for selective, rigid attachment to the corresponding handle connector 48a, 48b as described above (e.g., the cannula connector 66a, 66b and the corresponding handle connector 48a, 48b collectively form a locking mechanism), and thus can include or contain a luer-lock threaded fitting. Alternatively, the cannula connector 66a, 66b can be omitted, and depth markings (not shown) included along an exterior of the proximal region 64a, 64b that facilitate desired locating of the working end 62a, 62b relative to the corresponding cannula 22a, 22b as described below.

The working end 62a, 62b can include one or more components appropriate for forming a cavity or void within bone. For example, in some constructions, the working end 62a, 62b includes one or more expandable or inflatable members (e.g., a single balloon, multiple balloons, a single balloon with two or more discernable inflation zones, etc.) constructed to transition between a contracted (e.g., deflated) state in which the working end/balloon 62a, 62b can be passed through the corresponding lumen 44a, 44b, and an expanded (e.g., inflated) state in which the working end/balloon 62a, 62b expands and compacts contacted cancellous bone. In this regard, a size and shape of the working end/balloon 62a, 62b can be predetermined and/or restrained with one or more additional components (not shown), such as internal and/or external restraints. Regardless, the working end/balloon 62a, 62b is structurally robust, able to withstand (e.g., not burst) at expected inflation pressures and when in contact with bone. Further, the first working end 62a and the second working end 62b can be identical or different.

For reasons made clear below, at least one, and in some embodiments both, of the working ends/balloons 62a, 62b are optionally exteriorly coated with a material adapted or tailored to resist bonding with the curable material being delivered to the vertebra 30. The anti-sticking coating can assume various forms as a function of the selected curable material, and in some embodiments is a silicone coating. Other materials exhibiting adversion to bonding with bone cement are also envisioned, for example, polypropylene. In related embodiments, a thin-walled expandable sleeve constructed of the selected anti-sticking material (e.g., a polypropylene sleeve) can be disposed over the working end/balloon 62a, 62b. Though not shown, one or both of the cavity-forming devices 20a, 20b can include a valve or similar component that operates to selectively seal the working end/balloon 62a, 62b.

The cavity-forming devices 20a, 20b each further include one or more additional components connected or operable through the proximal region 64a, 64b for actuating the corresponding working end 62a, 62b. By way of one non-limiting example, then, each of the cavity-forming devices 20a, 20b can include a source 68a, 68b of pressurized fluid (e.g., contrast medium) for inflating the balloon(s) carried or formed by the corresponding working end 62a, 62b. A handheld, syringe-type pump can be used as the pressurized source. In other embodiments, a single one of the sources of pressurized fluid 68a or 68b can be provided and employed to inflate both of the working ends/balloons 62a, 62b individually.

Where provided, the optional delivery tube 14 is sized for insertion within the lumens 44a, 44b, and defines a distal tip 80 and a proximal section 82. As described below, the delivery tube 14 can be employed to deliver curable material to the target site. Thus, the delivery tube 14 has an outer diameter that is smaller than a diameter of the lumens 44a, 44b; however, the outer diameter of the delivery tube 14 should not be so small as to allow curable material to readily travel around the outside of the delivery tube 14 and back into the corresponding cannula 22a, 22b.

A cannula connector 84 is optionally coupled to, or formed by, the proximal section 82 of the delivery tube 14. The cannula connector 84 is akin to the optional cannula connector 66a, 66b described above (e.g., combines with the selected handle connector 48a, 48b to form a locking mechanism), and thus can assume any of the forms previously described. Alternatively, the delivery tube 14, where provided, can form depth markings (not shown) along the proximal section 82 that facilitates desired locating of the distal tip 80 relative to the cannula 22a, 22b during use.

The delivery tube 14 is configured for fluid coupling to the curable material source 16. In some embodiments, a portion of the delivery tube 14 projects proximally beyond the optional cannula connector 84, and is fluidly coupled to the curable material source 16, for example via an injection connector 86. Alternatively, auxiliary tubing 88 can be provided with the curable material source 16, and fluidly connected to the delivery tube 14 via the optional cannula connector 84. In yet other embodiments, the delivery tube 14 is omitted, and the curable material source 16 connected directly to the handle connector/proximal end 48a, 48b (e.g., the auxiliary tube 88 is connected to the connector 48a, 48b; or the tubing 88 eliminated and the curable material source 16 (e.g., a syringe) directly coupled to the connector 48a, 48b).

The curable material source 16 can assume various forms appropriate for delivering the desired curable material, and may typically comprise a chamber filled with a volume of curable material and employing any suitable injection system or pumping mechanism to transmit curable material out of the chamber and through the delivery tube 14. Typically, a hand injection system is used where a user applies force by hand to an injector. The force is then translated into pressure on the curable material to flow out of the chamber. A motorized system may also be used to apply force.

While the system 10 has been described as including the single source of curable material 16, in other constructions, a separate source of curable material 16 can be provided for each of the delivery assemblies 12a, 12b. Similarly, two (or more) of the optional delivery tubes 14 can be included. Along these same lines, the system 10 can alternatively be configured such that the curable material source 16 is directly connected to one or both of the cavity-forming devices 20a, 20b (e.g., the elongated body 60a of the first cavity-forming device 20a can form or terminate at a nozzle proximate (e.g., distal) the working end 62a and through which the curable material can be directly dispensed).

Regardless of an exact configuration, the system 10 in accordance with principles of the present disclosure is highly useful in performing a wide variety of height restoration and bone stabilization procedures as part of an overall curable material delivery procedure. To this end, FIG. 2A illustrates initial use of the system 10 in restoring the height of, and delivering curable material into, a target site of a vertebra 100. In general terms, the vertebra 100 includes pedicles 102a, 102b and a vertebral body 104 defining a vertebral wall 106 surrounding bodily material 108 (e.g., cancellous bone, blood, marrow, and soft tissue). The pedicles 102a, 102b extend from the vertebral body 104 and surround a vertebral foramen 110. As a point of reference, systems of the present disclosure are suitable for accessing a variety of bone sites. Thus, while the vertebra 100 target site is illustrated, it is to be understood that other bone sites can be accessed and treated by the system 10 (e.g., femur, long bones, ribs, sacrum, etc.).

The first and second cannulas 22a, 22b are initially employed to form first and second access paths to first and second target site locations 120a, 120b. For example, the cannulas 22a, 22b are inserted in a bipedicular fashion through respective ones of the pedicles 102a, 102b and into the bodily material 108. The cannulas 22a, 22b provide access to the corresponding target site 120a, 120b at the open distal ends 42a, 42b thereof. One or more stylets (not shown) can be employed to assist in forming/accessing the target sites 120a, 120b. For example, a series of differently-sized or configured (e.g., sharpened and blunt) stylets can be successively delivered through the respective cannula 22a, 22b to form a channel to the target site 120a, 120b. Alternatively, or in addition, an outer guide cannula (not shown) can initially be deployed to form an access path for subsequent insertion of the cannulas 22a, 22b.

Figure 2B:
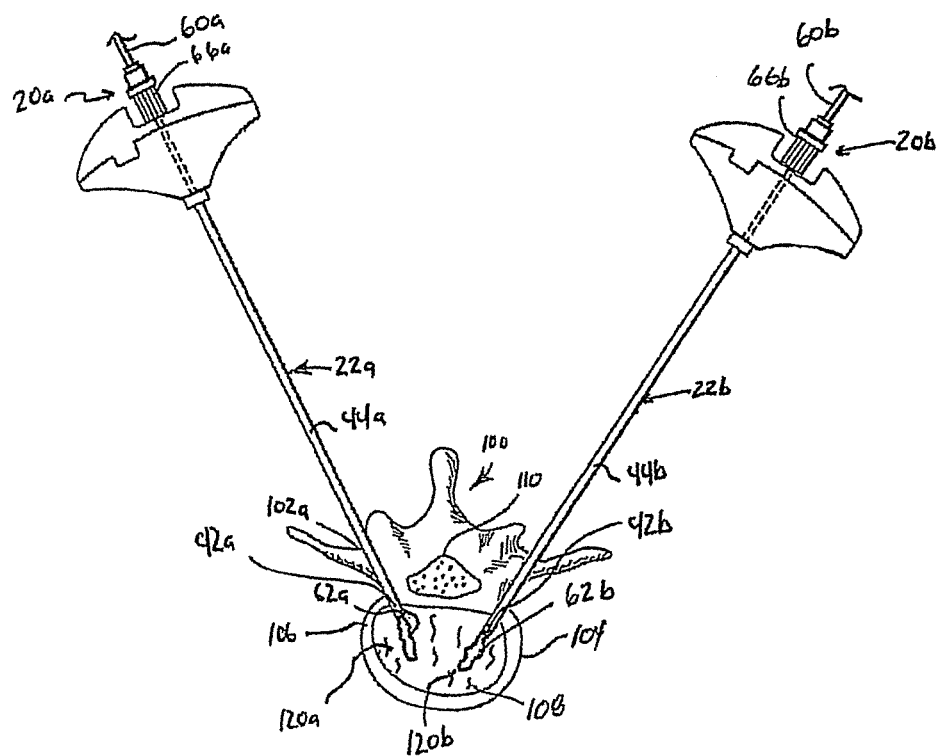

Once the cannulas 22a, 22b are positioned within the bodily material 108 at the desired target sites 120a, 120b, the cavity-forming devices 20a, 20b are assembled to the corresponding cannula 22a, 22b. For example, and as shown in greater detail in FIG. 2B, the elongated body 60a, 60b is slidably inserted within the corresponding cannula 22a, 22b, with the respective working end 62a, 62b being distally advanced therethrough. More particularly, with configurations in which the working end 62a, 62b is a balloon or other expandable member format, the working end/balloon 62a, 62b is transitioned to a contracted state (e.g., deflated) so as to be slidably received through the lumen 44a, 44b. The elongated body 60a, 60b is positioned relative to the corresponding cannula 22a, 22b such that the respective working end/balloon 62a, 62b extends distal the corresponding cannula distal end 42a, 42b. For example, where the elongated body 60a, 60b includes depth markings as described above, the appropriate depth marking is aligned with the corresponding handle connector 48a, 48b (FIG. 1), thereby ensuring that the working end/balloon 62a, 62b is fully deployed or extended beyond the corresponding cannula distal end 42a, 42b. In other constructions, upon connection of the optional cannula connector 66a, 66b and the corresponding handle connector 48a, 48b, the working end/balloon 62a, 62b is distal the corresponding distal end 42a, 42b and is positioned at the corresponding target site 120a, 120b. Regardless, placement of the cavity-forming devices 20a, 20b can be performed simultaneously or consecutively.

Figure 2C:
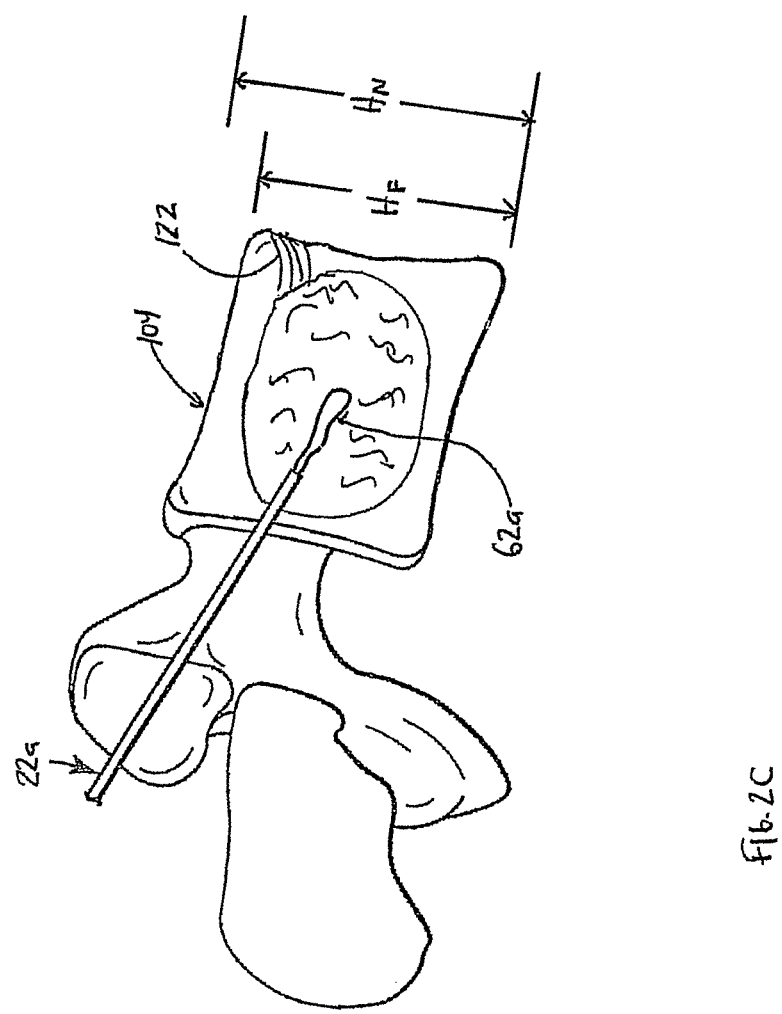
FIG. 2C is a lateral view of the vertebral body of FIGS. 2A and 2B.

As a point of reference, FIG. 2C provides a lateral view of the vertebral body 104 in which the first working end/balloon 62a has been deployed (and in the contracted state). As shown, the vertebral body 104 is fractured (referenced generally at 122) and thus exhibits a fractured height $H_F$ that is less than a natural or native height $H_N$ (designated generally).

Figure 3A:
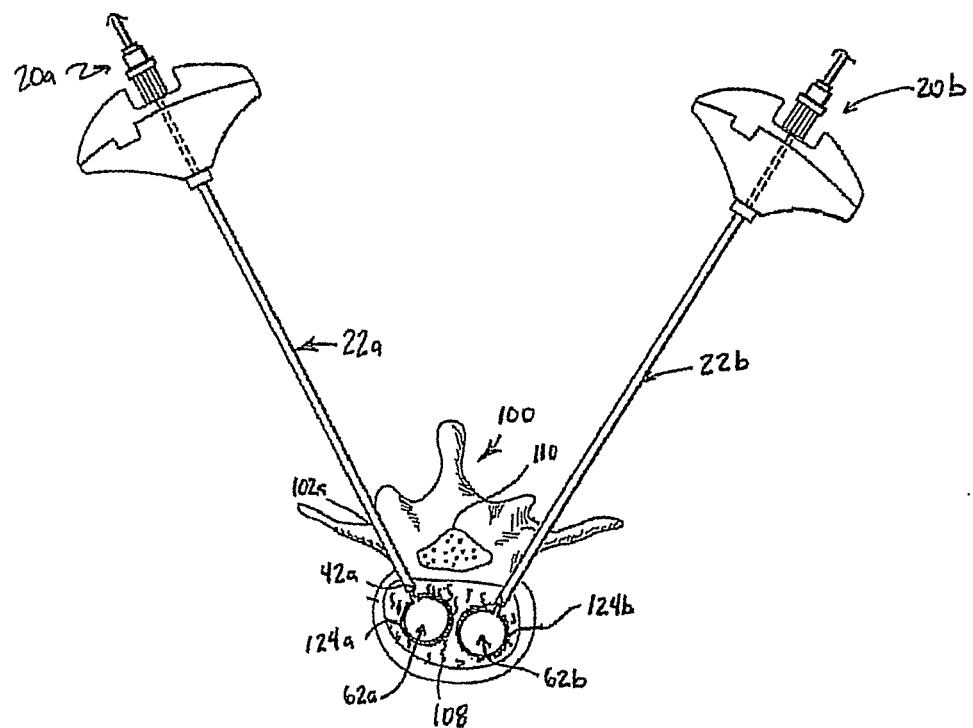

With reference to FIG. 3A, the cavity-forming devices 20a, 20b are operated to cause the corresponding working ends/balloons 62a, 62b to form first and second cavities or voids 124a, 124b, respectively, in the bodily material 108. For example, the working ends/balloons 62a, 62b can be expanded (e.g., inflated) substantially simultaneously. Alternatively, with embodiments in which a single inflation source 68a or 68b (FIG. 1) is provided, the first working end/balloon 62a is initially inflated and then sealed in the expanded or inflated state. The inflation source 68a or 68b is then fluidly connected to the second working end/balloon 62b and operated to cause expansion thereof. Following expansion of the working ends/balloon 62a, 62b, the expanded working ends 62a, 62b are both supporting the vertebral body 108. In this regard, and as best illustrated in FIG. 3B, expansion of the working ends/balloons 62a, 62b not only forms the cavities 124a, 124b, but also restores or enhances a height of the fractured vertebral body 104. More particularly, a restored height $H_R$ is established that beneficially approximates the natural height $H_N$. The restored height $H_R$ may be the same as, slightly less than, or slightly greater than, the natural height $H_N$ (FIG. 2C); regardless, the restored height $H_R$ is greater than the fractured height $H_F$ (FIG. 2C).

Figure 4A:
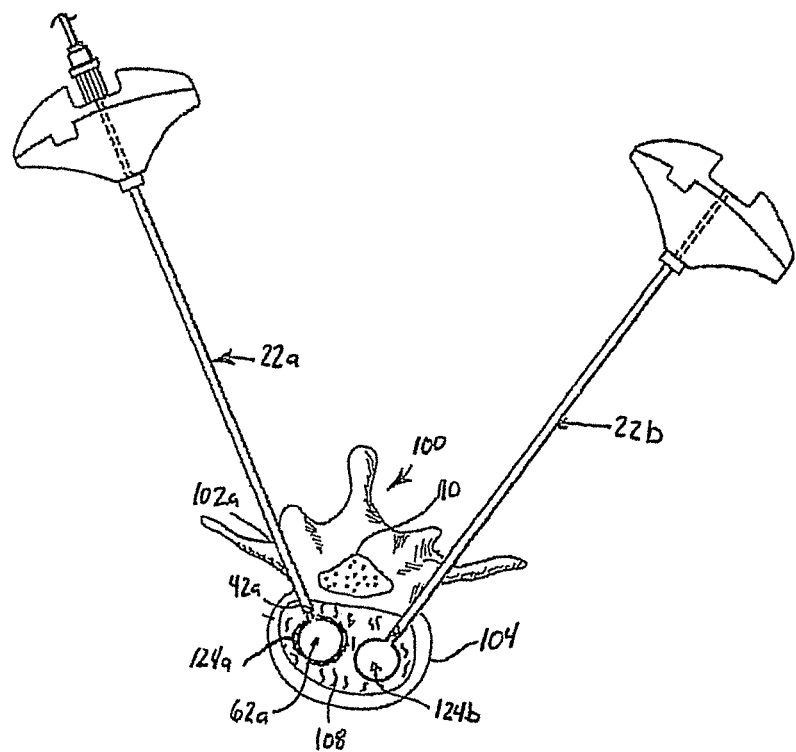
Figure 4B:
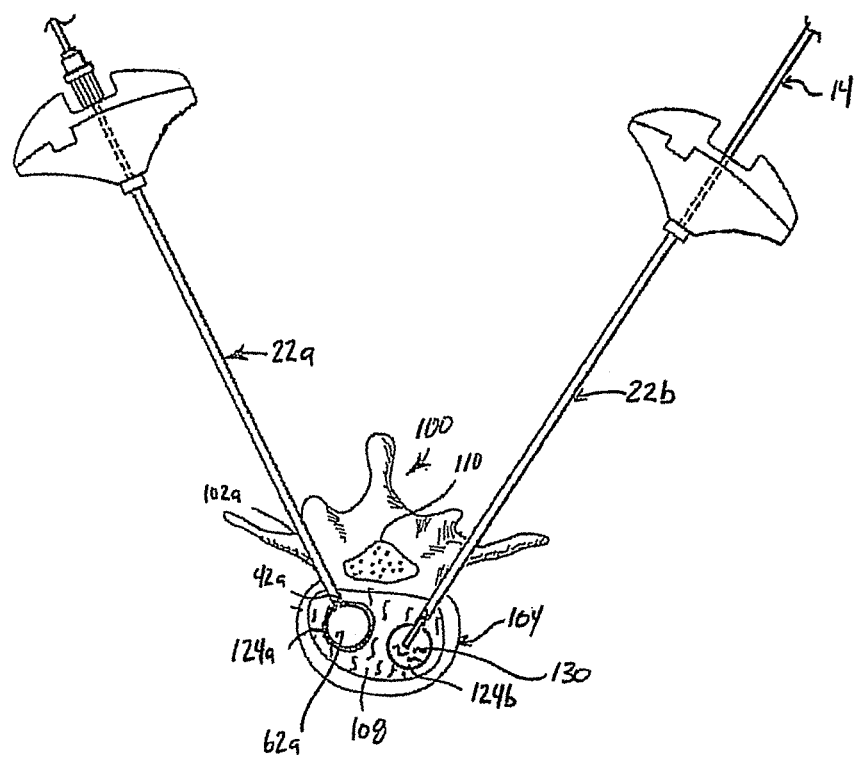

Returning to FIG. 3A, the second cavity-forming device 20b is then operated to transition the second working end/balloon 62b from the expanded state to the contracted state (e.g., the second balloon 62b is deflated). In the contracted state of the second working end/balloon 62b, the second cavity-forming device 20b can be removed from the second cannula 22b as shown in FIG. 4A. Subsequently, and with reference to FIG. 4B, the optional delivery tube 14 is disposed within the second cannula 22b, and the source of curable material 16 (FIG. 1) operated to deliver curable material 130 into the second cavity 124b. With other constructions, the delivery tube 14 is omitted and the curable material 130 is delivered to the second cavity 124b directly through the second cannula 22b. Once a desired volume of the curable material 130 has been delivered to the second cavity 124b, the delivery tube 14 (where provided) and optionally the second cannula 22b are removed from the patient. Throughout this portion of the procedure, the first working end/balloon 62a remains expanded and in place, maintaining the vertebral body 104 at the restored height $H_R$ (FIG. 3B). It will be understood that it is equally acceptable to reverse the order and instead initially fill the first cavity 124a with the curable material 130 (i.e., the first cavity-forming device 20a removed from the vertebral body 104 while the second working end/balloon 62b remains in place during subsequent dispensement of the curable material 130 into the first cavity 124a).

Figure 5:
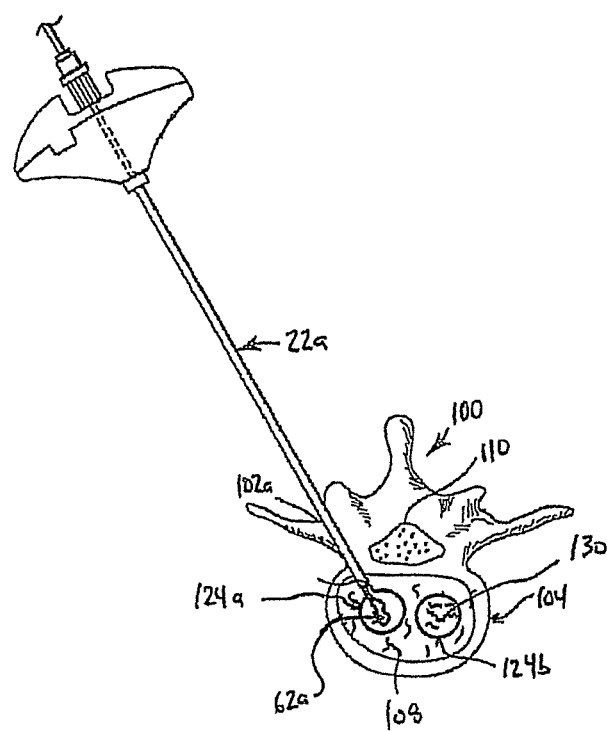
Figure 6:
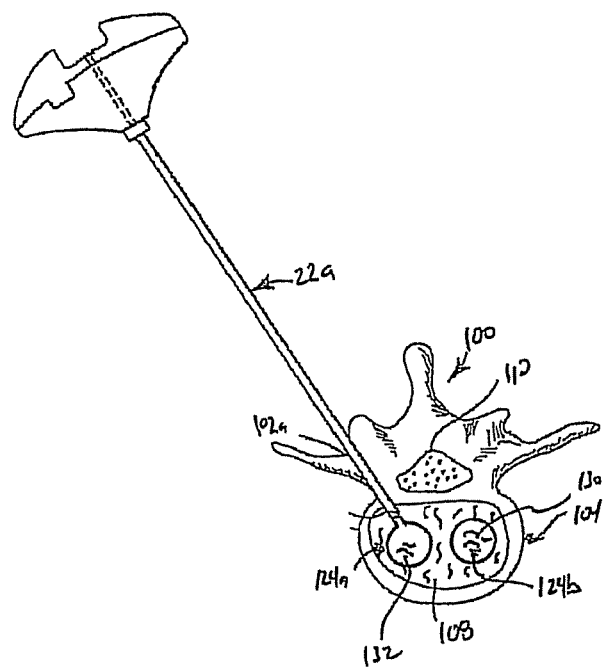

Once the curable material 130 within the second cavity 124b has sufficiently hardened or cured, the second cannula 22b can be removed and the first working end/balloon 62a is transitioned from the expanded state to the contracted state (e.g., the first balloon 62a is deflated) as shown in FIG. 5. In this regard, the hardened, curable material 130 in the second cavity 124b supports and maintains the vertebral body 104 at the restored height $H_R$ (FIG. 3B) while the first working end/balloon 62a is transitioned (e.g., deflated). Further, the optional anti-sticking coating on the first working end/balloon 62a resists bonding with the curable material 130 delivered to the second cavity 124b such that the hardened curable material 130 in the second cavity 124b will not prevent the first working end/balloon 62a from deflating should the curable material 130 come into contact with an exterior of the first working end/balloon 62a. Regardless, in the contracted state, the first cavity-forming device 20a can be removed from the patient, and is optionally replaced with the delivery tube 14. Finally, as shown in FIG. 6, curable material 132 is delivered into the first cavity 124a (either through the optional delivery tube 14 or directly through the first cannula 22a with embodiments in which the delivery tube 14 is omitted).

Systems and methods in accordance with the present disclosure provide a marked improvement over previous designs and techniques. By inflating and dispensing curable material in a step-wise fashion, the height of a fractured vertebral body (or other bone site of interest) can be restored and retained.

Although the present disclosure has been described with reference to preferred embodiments, workers skilled in the art will recognize that changes can be made in form and detail without departing from the spirit and scope of the present disclosure.

What is claimed is:

1. A method for stabilizing a fractured bone structure of a patient, the fractured bone structure having a fractured height, the method comprising:
    expanding the bone structure to a restored height greater than the fractured height by transitioning at least a first expandable member inserted into the bone structure from a contracted state to an expanded state;
    delivering a curable material into a first cavity formed in the bone structure while the first expandable member maintains the bone structure at the restored height;
    allowing the curable material to harden while the first expandable member maintains the bone structure at the restored height; and
    after the curable material has hardened, removing the first expandable member from the bone structure.

2. The method of claim 1, wherein the bone structure is a vertebra.

3. The method of claim 1, wherein a second cavity is defined in the bone structure following removal of the first expandable member, the method further comprising:
    delivering a curable material into the second cavity.

4. The method of claim 1, wherein the step of expanding the bone structure further includes transitioning a second expandable member inserted into the bone structure from a contracted state to an expanded state.

5. The method of claim 4, wherein the first and second expandable members are balloons.

6. The method of claim 1, wherein the first expandable member includes a balloon exteriorly coated with anti-sticking material.

7. The method of claim 1, wherein the step of delivering a curable material includes a portion of the curable material coming into contact with the first expandable member, and the step of allowing the curable material to harden includes the portion of the curable material in contact with the first expandable member not bonding to the first expandable member.

* * * * *